United States Patent [19]

Shuman

[11] Patent Number: 4,880,928

[45] Date of Patent: Nov. 14, 1989

[54] PROCESS FOR THE PREPARATION OF 3-((4-BROMO-2-FLUOROPHENYL)METHYL)-3,4-DIHYDRO-4-OXO-1-PHTHALAZINE-ACETIC ACID

[75] Inventor: Richard F. Shuman, Westfield, N.J.

[73] Assignee: Merck & Co., Inc., Rahway, N.J.

[21] Appl. No.: 197,481

[22] Filed: May 23, 1988

Related U.S. Application Data

[63] Continuation-in-part of Ser. No. 135,885, Dec. 21, 1987, abandoned.

[51] Int. Cl.[4] ............................................. C07D 237/32
[52] U.S. Cl. ...................................................... 544/237
[58] Field of Search .......................................... 544/237

[56] References Cited

U.S. PATENT DOCUMENTS 4,251,528  2/1981  Brittain et al. ...................... 544/237

Primary Examiner—Mark L. Berch
Attorney, Agent, or Firm—David L. Rose; Hesna J. Pfeiffer

[57] ABSTRACT

There is disclosed an improved process for the preparation of 3-[(4-bromo-2-fluorophenyl)-methyl]-3,4-dihydro-4-oxo-1-phthalazineacetic acid. The process is significantly improved over the prior art process in preparing the product in a one-step process where the prior art required three steps. The instant process directly alkylates a phthalazine ring nitrogen in the presence of the acetic acid moiety without the necessity of protecting the carboxylic acid group as was necessary in the prior art preferred process. The product is useful for treating the progressive deterioration resulting from diabetes.

22 Claims, No Drawings

PROCESS FOR THE PREPARATION OF 3-((4-BROMO-2-FLUOROPHENYL)METHYL)-3,4-DIHYDRO-4-OXO-1-PHTHALAZINE-ACETIC ACID

CROSS REFERENCE TO RELATED APPLICATIONS

This application is a continuation-in-part of application Ser. No. 135,885, filed Dec. 21, 1987, now abandoned.

BACKGROUND OF THE INVENTION

Certain phthalazine 4-yl acetic acid derivatives are disclosed in U.S. Pat. No. 4,251,528 to Brittain et al and such generic and specific disclosure includes 3 [(4-bromo 2 fluorophenyl)-methyl]-3,4 dihydro 4 oxo-1-phthalazineacetic acid. The process disclosed for the preparation of such compound generally involves the protection of the carboxylic acid group with the preparation of an ester thereof. Thus, the synthesis of the product involved the preparation of a lower alkyl ester of 3,4-dihydro-4-oxo-1 phthalazineacetic acid, the alkylation of the 3-position ring nitrogen to form the esterified product and deesterification to form the product. Three steps were thus involved and yields are stated to be about 36% overall for the alkylation and deesterification reactions. In the same Brittain et al reference one example is given of a direct alkylation of the unesterified carboxylic acid, however the yields are only about 15% or less. Additional attempts to prepare the above product using the unesterified carboxylic acid and the conditions described in Brittain et al have resulted in the preparation of negligible amounts of the product. The instant improved process involves direct alkylation of the unprotected carboxylic acid. It thus avoids the time and expense of esterification and deesterification and most surprisingly, directly produces the desired compound in yields approaching 90%.

SUMMARY OF THE INVENTION

This invention is concerned with an improved process for the preparation of 3 [(4 -bromo-2 -fluorophenyl)methyl]3,4-dihydro 4 oxo-1-phthalazineacetic acid. This compound is also identified as ponalrestat. The process improvement comprises the direct alkylation of the phthalazineacetic acid starting material without formation and removal of the ester protecting group, and the concomitant careful maintenance of solvent and pH conditions, to provide yields of approximately 85 to 90% or greater, which comprises a nearly six fold (600%) improvement over the prior art. Thus, it is an object of the instant invention to describe the improved process for the preparation of the compound. A further object is to describe the specific reaction conditions which afford the surprising improvement in yields. It is a still further object of this invention to describe the solvents and basic reagents which afford the surprising increases in yields. Further objects will become apparent from a reading of the following description.

DESCRIPTION OF THE INVENTION

The Brittain et al reference describes two methods for the preparation of 3-[(4-bromo 2 fluorophenyl)methyl]3,4 dihydro 4 oxo-1 phthalazineacetic acid and similar compounds. The more successful of the two processes involves the protection of the carboxylic acid group of the acetic acid moiety by making the ester thereof. The ring nitrogen is then alkylated in the presence of a base with a ring substituted benzyl bromide compound following which the ester group is removed by hydrolysis achieving yields of up to about 36% overall for the two reactions. The other process described involves the direct alkylation of the ring nitrogen without protecting the carboxylic acid group in the presence of sodium hydroxide as a base, however with such a process the yields are only about 15%.

The above product has become of great interest as an agent to combat the long term debilitating effects of diabetes on the microvascular system with often devastating effects on the renal, neural and optic systems of the afflicted patient. Thus more economical and efficient processes for the preparation of the compound are being sought.

The improved one step process for the preparation of the above compound is outlined in the following reaction scheme:

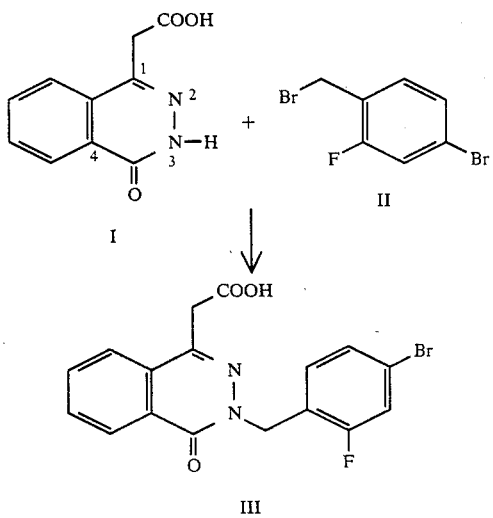

The reaction conditions which result in the surprising increases in yields and reduction in time and expense in the preparation of the product, Compound III, involve the reaction of 3,4 dihydro-4-oxo 1-phthalazineacetic acid (I), with 4 bromo-2-fluorobenzyl bromide (II) in a protic polar solvent, an aprotic polar solvent or a mixture of a protic polar solvent with an aprotic polar solvent and a tetraalkyl or phenyl substituted tetraalkyl ammonium hydroxide as the base. The preferred protic polar solvents are lower alkanols such as methanol, ethanol, 1-propanol, 2 propanol and the like. Preferred aprotic polar solvents are N,N-dimethylformamide (DMF), acetonitrile, dimethylsulfoxide, N,N-dimethylacetamide, N-methylpyrrolidine and the like. Preferred tetraalkyl and phenyl substituted tetraalkyl ammonium hydroxide compounds are tetramethylammonium hydroxide, tetraethyl ammonium hydroxide, tetrabutylammonium hydroxide, benzyl trimethylammonium hydroxide, cetyl trimethylammonium hydroxide, tricaprylmethylammonium hydroxide and the like.

The most preferred protic polar solvent is 2-propanol; the most preferred aprotic polar solvent is N,N dimethylformamide and the preferred base is tetramethylammonium hydroxide.

The preferred solvent system is a mixture of a protic polar solvent and an aprotic polar solvent, most preferably in the range of about 2:1 to 1:2.

Compound II may be utilized as a solution in a solvent non reactive to the instant reaction conditions such as a chlorinated hydrocarbon preferably chlorobenzene, or toluene, 2 propanol, hexane, cyclohexane and the like, or Compound II may be crystallized and utilized as a solid reagent. The reaction is carried out at from 0° C. to about 80° C., preferably at room temperature, and it is generally complete in from 15 minutes to 24 hours, although most reactions are complete from about 15 minutes to 4 hours.

The reaction is carried out using one equivalent of Compound I and from 0.8 to 1.3 equivalents of Compound II. It is preferred to use approximate molar equivalents of each of the reactants. The tetraalkyl ammonium hydroxide is used in at least two molar equivalents relative to Compound I and preferably from 2.0 to 2.1 molar equivalents. A large excess of the ammonium compound has not been found to be advantageous. To prepare the product, Compound I is dissolved in the chosen solvent system and combined with the tetraalkyl ammonium hydroxide at about room temperature for sufficient time to prepare the dianion of the carboxylic acid and of the 3 position ring nitrogen. Generally about 10 minutes or less is required. Then Compound II is added neat or dissolved in a non reactive solvent and the reaction mixture proceeds, either with or without stirring for the selected time and temperature. The product, Compound III, is isolated from the reaction mixture by quenching the reaction in water, or ice water and washing the aqueous layer with non polar organic solvents, preferably hydrocarbons such as hexane, cyclohexane and the like. Acidification of the aqueous layer will crystallize the product which may be further purified using techniques known to those skilled in the art.

The following examples are provided in order that the instant invention may be more fully understood. They should not be construed as limiting the invention.

EXAMPLE 1

Following the procedure described in Example 1 of U.S. Pat. No. 4,251,528 (Brittain, Wood), 3,4 dihydro-4-oxo-1-phthalazineacetic acid (I, 2.0 g, 9.8 mmole) was added to a solution of sodium hydroxide (0.9 g, 22.5 mmole) in methanol (50 mL). To this solution was added (2.8 g, 10.4 mmole) of 4 bromo 2 fluorobenzyl bromide (II). After 3 hours at reflux the mixture wa cooled and assayed by HPLC which showed the presence of a 6.7% yield of III. Assay by gas-liquid chromatography and mass spectral analysis showed the presence of a large amount of 4 bromo-2 fluorobenzyl methyl ether arising from reaction of the methanol solvent with II. Product III was not isolated.

EXAMPLE 2

Under nitrogen, 41.0 g (0.20 mole) of 3,4 dihydro 4-oxo 1-phthalazineacetic acid (I) was added to 280 ml of anhydrous N,N-dimethylformamide. To this was added 217 ml of a solution of 38.9 g (0.42 mole) of tetramethylammonium hydroxide in 2-propanol. To the resulting solution was added a solution of 4 bromo 2 fluorobenzyl bromide (II) (52.8 g, 0.197 mole) in 190 ml of chlorobenzene over 30 minutes at 25°-30° C. About 30 minutes after the addition of II was complete, liquid chromato graphic analysis indicated the presence of about 94% of product (III). The reaction was aged at 25° C. for 2 hours and then diluted with 350 mL of water. The aqueous layer was washed with 250 mL of cyclohexane. The organic layer was back washed with 100 mL of water.

The product containing aqueous layer was adjusted to pH 7 with phosphoric acid, treated with 6.2 g of decolorizing carbon for 30 minutes andhen filtered through a bed of 6.2 g of filter aid. The cake was washed with the 100 ml of aqueous backwash from above. The combined aqueous filtrate and wash was then acidified with phosphoric acid to pH 6.3 and seeded with 0.10 g of product. Heavy crystallization occurred. The pH was brought to 4.5 over one hour with phosphoric acid. The crystalline slurry was cooled to 0°-5° C. and aged at 0°-5° C. for 2 hours. The product was filtered, washed with 200 mL of cold water and dried to give 72.5 g (94% yield of product (III)), having a purity of 94.5%. The yield corrected for purity was 68.6 g (89%). The melting point was 173°-177° C. with decomposition. When recrystallized from methanol, or from a mixture of water and methyl ethyl ketone, a denser crystalline form was obtained with a melting point at 184°-186° C. with decomposition. The recovery of pure product from a mixture of water and methyl ethyl ketone was 93%.

EXAMPLE 3

Using a procedure similar to that described in Example 2, except that 2 propanol was substituted for DMF, a yield of 86% of III was measured by HPLC 30 minutes after addition of II was complete. Isolation gave 68 g (87%) of product (m.p. 174°-185° C. with decomposition) having a purity of 96%. Thus, the yield corrected for purity was 65 g (84%). Five grams of this material was heated for 30 minutes in refluxing acetone (50 mL) to afford 4.6 grams (92% recovery) of pure product, m.p. 185°-187° C. with decomposition.

EXAMPLE 4

Using a procedure similar to that described in Example 3 except that 0.42 moles of tetramethyl ammonium hydroxide was used as a 20% solution in methanol (217 mL) the presence of about 84% of product was measured by HPLC 30 minutes after addition of 4 bromo 2 fluorobenzyl bromide. The product was not isolated.

EXAMPLE 5

Using a procedure similar to that described in Example 3, except that 0.42 moles of tetrabutyl ammonium hydroxide was used as a 55% solution in water in place of tetramethylammonium hydroxide in propanol and 4 bromo 2 fluorobenzyl bromide (II) in 2 propanol rather than in chlorobenzene was added, so that a yield of 64% of III was measured by HPLC after addition of II was complete. The product was not isolated.

EXAMPLE 6

Using a procedure similar to Example 2, except that solid tetramethylammonium hydroxide pentahydrate (0.42 moles) in DMF was used in place of tetramethylammonium hydroxide in 2 propanol, a yield of about 87.5% of III was measured by HPLC after addition of II was completed. The product was not isolated.

EXAMPLE 7

Using a procedure similar to that described in Example 5, except that 0.42 moles of tetrabutylammonium hydroxide was used as an anhydrous solution in 2-propanol (217 mL) in place of tetramethyl ammonium hydroxide in propanol, and 4 bromo 2 fluoro benzyl bromide (II) was dissolved in 2-propanol rather than in chlorobenzene to afford a 30% yield of III as measured by HPLC. The product was not isolated.

By way of further illustrating the advantages of tetraalkyl ammonium hydroxides for direct 4 bromo 2-fluorobenzylation of unprotected and underivatized I, especially in an optimized mixture of solvents, the results of preceeding Examples 1–7 are collected in the following Table I and contrasted with Example 1 from U.S. Pat. No. 4,251,528.

with a compound of the formula

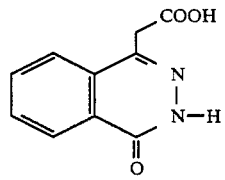

TABLE I

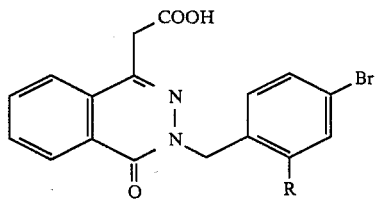

| Example | R | Base (mole ratio relative to I) | Solvent | Solvent for II | Percent Yield HPLC Assay | Percent Yield Isolation |
|---|---|---|---|---|---|---|
| (1) | H | NaOH (2.3) | Methanol | Methanol | — | 16 |
| 1 | F | NaOH (2.3) | Methanol | — | 6.7 | — |
| 2 | F | (CH₃)₄NOH(2.1) | DMF-2-Propanol | Chlorobenzene | 94 | 89* |
| 3 | F | (CH₃)₄NOH(2.1) | 2-Propanol | Chlorobenzene | 86 | 84* |
| 4 | F | (CH₃)₄NOH(2.1) | DMF-Methanol | Chlorobenzene | 84 | — |
| 5 | F | (n-C₄H₉)₄NOH(2.1) | Water | 2-Propanol | 64 | — |
| 6 | F | (CH₃)₄NOH.5H₂O (2.1) | DMF | Chlorobenzene | 87.5 | — |
| 7 | F | (n-C₄H₉)₄NOH(2.1) | 2-Propanol | — | 30 | — |

(1) Brittain et al., U.S. Pat. No. 4,251,528, Example.
*Corrected for purity.

What is claimed is:

1. A process for the preparation of a compound of the formula

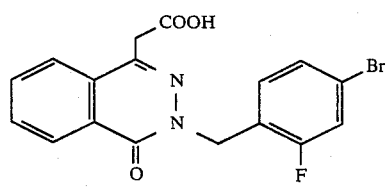

which comprises reacting a compound of the formula in a protic polar solvent, an aprotic polar solvent, or a mixture of a protic polar solvent and an aprotic polar solvent in the presence of a tetraalkyl or phenyl substituted tertraalkyl ammonium hydroxide.

2. The process of claim 1 wherein the tertiary alkyl or phenyl substituted tetraalkyl ammonium hydroxide is tetramethyl ammonium hydroxide, tetraethyl ammonium hydroxide, tetrabutyl ammonium hydroxide, benzyl trimethyl ammonium hydroxide, cetyltrimethylammonium hydroxide or tricaprylmethyl ammonium hydroxide.

3. The process of claim 2 wherein the tetraalkyl ammonium hydroxide is tetramethyl ammonium hydroxide.

4. The process of claim 1 wherein the protic polar solvent is a lower alkanol.

5. The process of claim 4 wherein the protic polar solvent is methanol, ethanol, 1 propanol or 2 propanol.

6. The process of claim 3 wherein the protic polar solvent is 2 propanol.

7. The process of claim 1 wherein the aprotic polar solvent is N,N dimethylformamide, acetonitrile, dimethylsulfoxide, N,N-dimethyl acetamide or N methylpyrrolidine.

8. The process of claim 7 wherein the aprotic polar solvent is N,N dimethylformamide.

9. The process of claim 1 wherein a mixture of protic and aprotic polar solvents is used.

10. The process of claim 9 wherein the ratio of protic to aprotic polar solvents is from about 2:1 to 1:2.

11. The process of claim 10 wherein the protic polar solvent is 2-propanol and the aprotic polar solvent is N,N dimethylformamide.

12. The process of claim 1 wherein Compound II is dissolved in a non reactive solvent.

13. The process of claim 12 wherein the non-reactive solvent is a chlorinated hydrocarbon, toluene, 2 propanol, hexane, or cyclohexane.

14. The process of claim 13 wherein the chlorinated hydrocarbon is chlorobenzene.

15. The process of claim 1 wherein the reaction is carried out at from 0° to 80° C.

16. The process of claim 15 wherein the reaction is carried out at about room temperature.

17. The process of claim 1 wherein from 0.8 to 1.3 moles of Compound II are employed for each mole of Compound I.

18. The process of claim 17 wherein approximately equimolar quantities of Compounds I and II are employed.

19. The process of claim 1 wherein at least two moles of the tetraalkyl ammonium hydroxide are employed for each mole of Compound II.

20. The process of claim 19 wherein from 2.0 to 2.1 moles of the tetraalkyl ammonium hydroxide are employed for each mole of Compound I.

21. The process of claim 1 wherein the reaction mixture proceeds for from 15 minutes to 24 hours following the combination of Compounds I and II.

22. The process of claim 21 wherein the reaction proceeds for from 15 minutes to 4 hours.

* * * * *